United States Patent
Legro et al.

(10) Patent No.: US 7,003,914 B2
(45) Date of Patent: Feb. 28, 2006

(54) METHOD FOR THE PROTECTION OF GERMINATING SEED AND PESTICIDE-COATED PELLETS

(75) Inventors: Robert Jean Legro, Enkhuizen (NL); Sijbert Honkoop, Maasdijk (NL)

(73) Assignee: Incotec International B.V., BL Enkhuizen (NL)

( * ) Notice: Subject to any disclaimer, the term of this patent is extended or adjusted under 35 U.S.C. 154(b) by 0 days.

(21) Appl. No.: 10/765,475

(22) Filed: Jan. 28, 2004

(65) Prior Publication Data

US 2004/0237395 A1   Dec. 2, 2004

Related U.S. Application Data

(63) Continuation of application No. 09/806,949, filed as application No. PCT/NL00/00523 on Apr. 3, 2001, now abandoned.

(30) Foreign Application Priority Data

Aug. 26, 1999 (NL) .................................. 1012918

(51) Int. Cl.
*A01C 1/00* (2006.01)
*A01C 1/06* (2006.01)

(52) U.S. Cl. ............... 47/58.1 SE; 47/57.6; 47/DIG. 9; 47/DIG. 11

(58) Field of Classification Search ................. 47/57.6, 47/58.1 SE, DIG. 9, DIG. 11
See application file for complete search history.

(56) References Cited

U.S. PATENT DOCUMENTS

| | | | | |
|---|---|---|---|---|
| 2,656,649 A | * | 10/1953 | Ostier | 47/57.6 |
| 3,600,830 A | * | 8/1971 | Hamrin | 47/57.6 |
| 3,651,772 A | * | 3/1972 | Garabedian | 111/200 |
| 3,950,891 A | * | 4/1976 | Hinkes | 47/57.6 |
| 4,198,782 A | * | 4/1980 | Kydonieus et al. | 47/58.1 R |
| 4,759,151 A | * | 7/1988 | Gerber | 47/57.6 |
| 4,808,430 A | * | 2/1989 | Kouno | 427/4 |
| 4,971,796 A | * | 11/1990 | Sjogren | 424/417 |
| 5,044,518 A | | 9/1991 | Sakaue et al. | |
| 5,068,105 A | * | 11/1991 | Lewis et al. | 424/93.3 |
| 5,130,171 A | * | 7/1992 | Prud'Homme et al. | 427/213.36 |
| 5,389,115 A | * | 2/1995 | Legro | 47/57.6 |
| 5,623,781 A | * | 4/1997 | Legro | 47/57.6 |

FOREIGN PATENT DOCUMENTS

| | | |
|---|---|---|
| CA | 1 143 651 | 3/1983 |
| CA | 1143651 | * 3/1983 |
| DE | 43 43 176 | 6/1995 |
| WO | WO 88/05625 | 8/1988 |

* cited by examiner

*Primary Examiner*—Peter M. Poon
*Assistant Examiner*—Andrea M. Valenti
(74) *Attorney, Agent, or Firm*—Nath & Associates PLLC; Gary M. Nath; Tanya E. Harkins

(57) ABSTRACT

The invention relates to a method for the protection of germinating seed from pesticide, wherein seed-containing pellets and pesticide-containing pellets are sown separately but simultaneously. According to a preferred embodiment of the invention, the pesticide-containing pellets have substantially the same shape and diameter as the seed-containg pellets, and the pesticide-containing pellets comprise the exact dosis of pesticide that is sufficient for one seed germ. Generally, the pellets with pesticide have a diameter ranging from 0,5–5.0 mm

9 Claims, 3 Drawing Sheets

METHOD FOR THE PROTECTION OF GERMINATING SEED AND PESTICIDE-COATED PELLETS

This is a Continuation Application of U.S. patent application Ser. No. 09/806,949 filed Apr. 3, 2001, now abandoned which is a 371 of PCT/NL00/00523 filed Jul. 24, 2000, and claims priority to The Netherlands application no. 1012918 filed Aug. 26, 1999, the entire contents of which are hereby incorporated by reference in their entirety.

The present invention relates to a method for the protection of germinating seed coated with pesticide.

Such a method is known in the field. Usually pesticides, such as, for example insecticides and fungicides are incorporated in the coatings of pelleted seeds.

The problem with many pesticides is that they can be rather phytotoxic for the germinating seed to which the pesticide is applied. One reason for this is the high dosage in which the pesticide often must be applied to afford adequate protection against the pest to be fought. The negative effect may vary from retarted germination abnormal seedlings, or even to a total lack of germination of part of the seeds. Of course, the degree in which germination may be affected so negatievely depends also on the type of pesticide, the seed species,the sensitivity of the variety, the vigour of the seed batch, and the environmental conditions during germination and emergence of the treated seed.

By covering the seed with a coating, the negative effect of the pesticide on the seed can be limited to some extend. For instance, the seed may be coated (pelleted) with a relatively thick layer of inert material on which the pesticide is applied in such a way that the pesticide is not directly in contact with the seed.

However, a further disadvantage of this method of pelleting is that at high dosages such a coating affords insufficient protection against the possible phytotoxic effect-of the pesticide. Furthermore, due to the high dosages the coating's physiochemical properties may be changed significantly, indirectly producing a negative effect due to a change in the oxygen/water balance in the coating.

The present invention has the aim to avoid these disadvantages. This aim is achieved according to the present invention by simultaneously sowing seed-containing pellets and pesticide-containing pellets as separate pellets.

Because the seed germ and the pesticide are incorporated in separate pellets, the seed in the seed-containing pellet can germinate and grow before it comes into contact with the pesticide which will be released from another pellet. Thus during the most vulnerable stage, the moment of germination, there is no contact yet with the pesticide.

It is noted that in the present invention the. term pesticide-containing pellets also includes film-coated inert cores (see example 3).

According to a prefered embodiment of the invention, the pesticide-containing pellets have substantially the same size and shape as the seed-containing pellets.

Since the pesticide-containing pellets are substantially the same size as the seed-containing pellets, it is thus possible with precision sowing machinery to sow one pesticide-containing pellet per plant. Thus in a simple way both sub-and overdose can be effectively avoided.

According to a preferred embodiment of the invention the pesticide-containing pellets comprise a pesticide dosage which is sufficient for-one seed germ.

Thus unnecessary waste of the expensive pesticide is avoided, and furthermore there is the least possible impact on the environment.

According to another aspect of the method of the present invention, the pesticide-containing pellets contain a filler material.

By supplementing the exact dosage of pesticide with an appropriate amount of filler material, the size of the pesticide-containing pellet can be adapted to that of the seed-containing pellet.

According to an advantageous embodiment of the invention, both pesticide-and seed-containing pellets have a substantially uniform diameter ranging from of 0.5–5 mm.

The invention also relates to a pesticide-containing pellet for use in combination with a seed-containing pellet.

By sowing pellets having the same shape and size, an optimal sowability with precision sowing machines can be achieved.

According to the invention, the pesticide in the pesticide-containing pellet may be, for example, acaricides or miticides, bactericides, fungicides, herbicides, insecticides (e.g. Rovral® (Rhone Poulenc), Gigant® (DowElanco), Gaucho® (Bayer), Oncol® (Luxan), mundial® (Rhone Poulenc), Birlane® (Cyanamid) etc.), molluscicides, nematicides and rodenticides are used but also growth hormones, nutrients, germination stimulants, micro organisms, pheromones, biological preparations, etc.

All types of filler material commonly used in the seed coating business can be used such as, for example, clay, perlite, diatomaceous earth, quartz, cellulose, vermiculite, mica, etc.

Naturally the pesticide-containing pellet may be produced in any desired shape and size depending on the seed-containing pellets to be sown at the same time.

The core of the pesticide-containing pellet according to the invention may be inert, for example, a glass-bead, perlite, plastic, pumice or any other suitable material. If desired however, it is also possible to use killed, non-germinating seed (for example killed by heat treatment, gamma rays, microwave etc.) or other bio-degradable organic material which has no detrimental effect on the seed germination.

Optionally according to the invention, a substance may be added to the pesticide-containing pill to regulate the release of the pesticide.

The present invention will now be further elucidated with reference to a number of exemplary embodiments. FIGS. 1–4 show alternative embodiments of a pesticide-containing pellet according to the invention.

FIG. 1 shows a pesticide-containing pellet 1 with a core 2, which core is surrounded by the active material 3.

FIG. 2 shows a pesticide-containing pellet 1 with a core 2, which core 2 is surrounded by a filler 4 provided with a coating of active material 3

FIG. 3 shows a pesticide-containing pellet 1 with a core, core 2 is surrounded by an active material 3 provided with a coating of filler 4.

FIG. 4 shows a pesticide-containing pellet 1 with a core 2, which core is covered successively with a layer of filler 4, a layer of active material 3 and a coating of filler 4.

Naturally the pesticide-containing pellets may have any shape as long as this shape substantially resembles the shape of the-seed-containing pellets.

The invention will now be elucidated with reference to a number of non-limiting examples.

EXAMPLE 1

One million lettuce seeds (lactuca sativa) in a batch-weighing 1,10 gram per 1 thousand grains were killed by means of gamma-rays (40 kGy). The batch was pelleted according to the standard procedure, using a standard 100 cm diameter pelleting-pan (Vingerlings Machinefabriek b.v., Rotterdam, Netherlands).

This process entailed the alternating addition of coating material (C-1, Incotec) and binding solution (Sol-1, Incotec) providing pellets having a uniform shape and size (3.25–3.5 mm slot screen).

Then the pellets were-dried for 1.5 hours at 40° C. In a fume-cupboard, at room temperature, 2000 ml of a commercial coating-formulation (Disco Color Red L083) was mixed with 1143 g of insecticide powder Gaucho 70 WS® (Bayer) and 2660 ml water. The batch of 1 million dried pellets was processed in a Pancoater (Ramacota 36) of a diameter of 36 inches according to the standard process.

Figure 2:
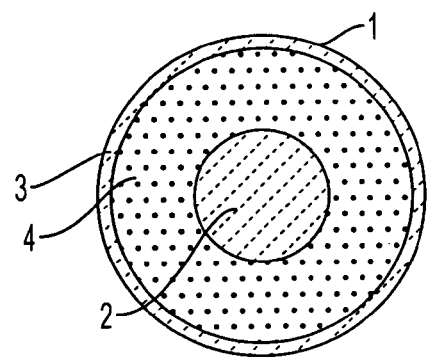
Figure 3:
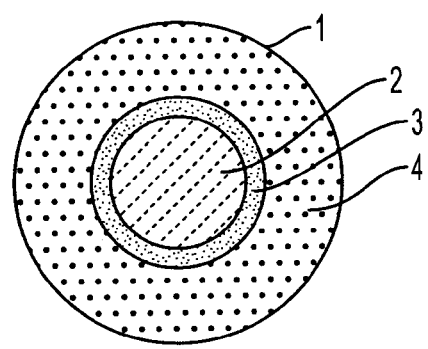

This process entailed that during the entire process (120 min.) the coating-mixture was evenly and slowly distributed over the pellets while continuously drying (drying temperature=55° C.), resulting in the pellets as described in FIG. 2. The insecticide is comprised in the thin film of coating on the outside of the pellet.

The above-mentioned pellets have a recovery of 98% (recovery measurements done by a HPLC) of the active ingredient imidacloprid, the active component (a.c.) of the Gaucho-formulation measuring a distribution coefficient of variation of 10%.

Figure 5:
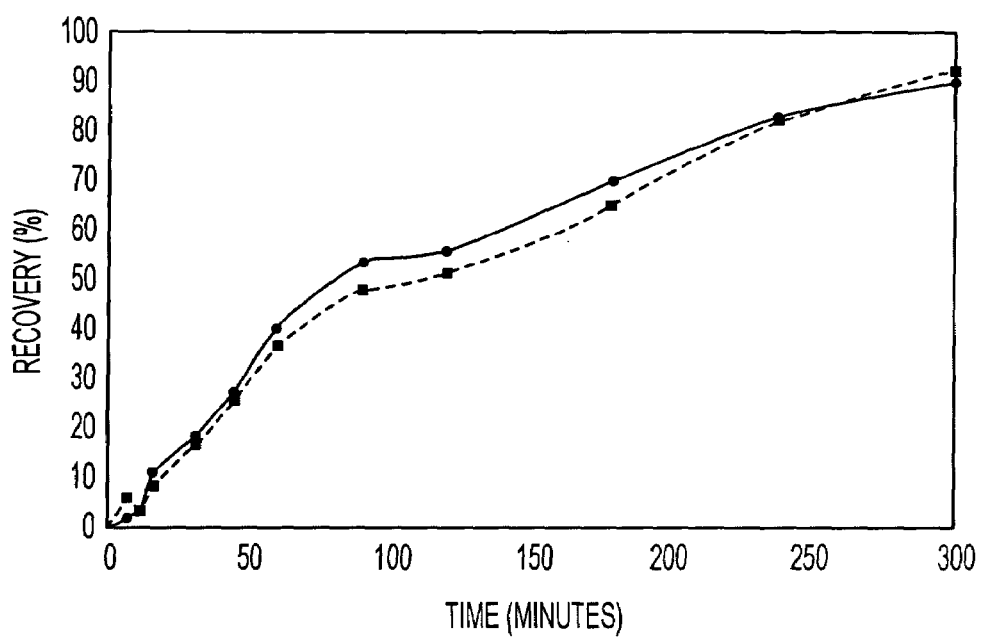
FIG. 5 shows a graph which illustrates the, release of active component from a (viable) seed-containing pellet according to the prior art (solid line) in comparison with a pellet according to the present. invention (dotted line).

The insecticide is released into the water from the produced Gaucho-pellets (800 g a.c./million pills) in the same way as from the pellets comprising both the seed and the Gaucho (800 gram a.c./million pellets) in the same pellet (see FIG. 5).

FIG. 5. shows the release into water of the active component from a viable seed-containing pellet according to the prior art (solid line) and from a pellet according to the invention (dotted line). Plotted are the recovery in % against time (minutes).

Figure 6:
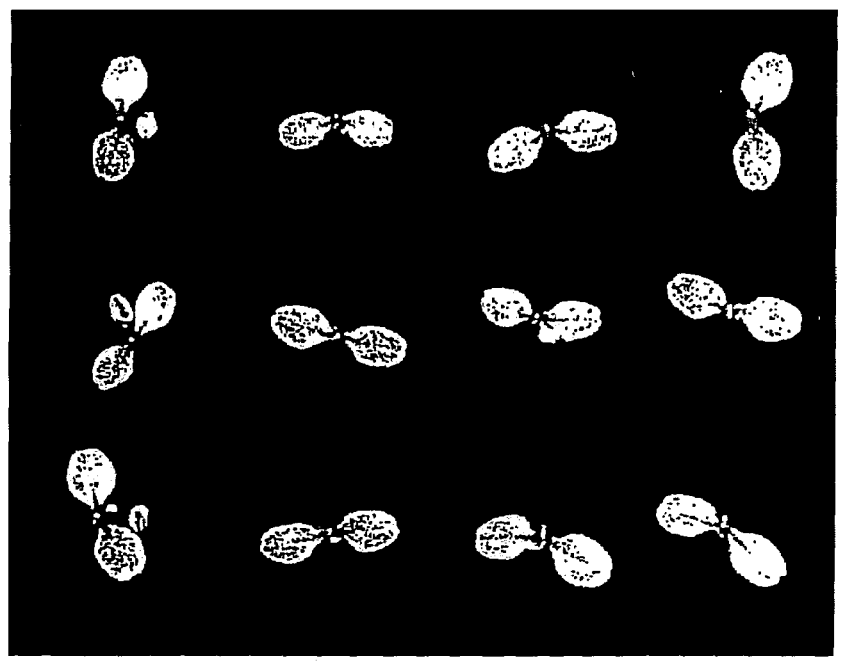
FIG. 6 shows germinated lettuce-seedlings from seed-containing pellets sown separately but simultaneously. with pesticide-containing pellets (present invention).
Figure 7:
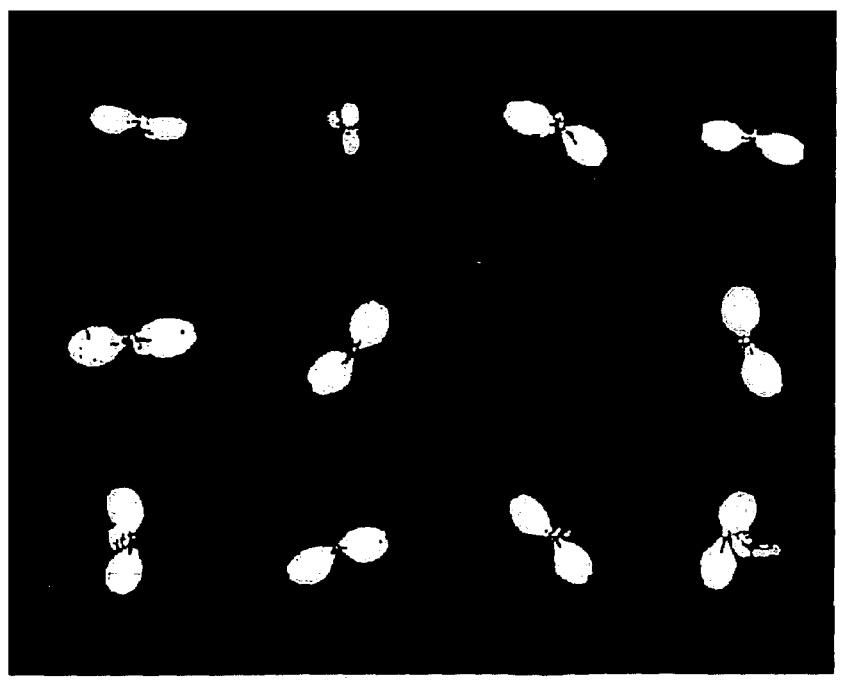
FIG. 7 shows germinated lettuce seedlings from pellets containing both seed and pesticide (prior art).

The seed-containing pellets and the Gaucho-containing pellets (800 gram a.c./million pellets) sown as separate pills (FIG. 6) germinate more evenly than the pellets that contain both live seed and Gaucho (800 g a.c./million pellets) in one pellet (see FIG. 7).

The above example is also applicable to other seed species, such as:

Tobacco (Nicotiana tabacum) in the pellet size 1.75–2.00 mm with a dosis of 200 g imidacloprid/million pellets.

Sugar beet (Beta Vulgaris) in the pellet size 3.75–4.50 mm with a dosis of 900 g imidacloprid/million pellets.

EXAMPLE 2.

From a batch of three million glass-beads pellets were produced according to the standard procedure. The batch was processed in a pelleting pan with a diameter of 100 cm (Vingerlings Machinefabriek b.v., Rotterdam, Netherlands). In this method the coating material (C-22, Incotec) and binding solution (Sol-1, Incotec) were added alternately in order to produce pellets of homogeneous size and shape (1.50–1.75 mm slot screen).

Subsequently, the pellets were dried at 60° C. for 45 minutes. In a fume-cupboard at room temperature 31.5 ml of a commercial coating formulation (Disco Color Red L083, Incotec) was mixed with 18.0 gram of insecticide powder Gaucho 70 WS® Bayer) en 10.4 ml of water. A batch of 90.000 dry pellets was placed in a 'Rotostat coating machine' with a diameter of 30 cm (Marline, Norfolk, England). The mixture of insecticide and coating formulation was applied by means of the standard 'spinning disc' (6 cm diameter). After 3 minutes process time, the mixture was distributed evenly over the pellets and the pellets were transferred to a standard pelleting pan. Alternately, finishing-material. (F-13, Incotec) and binding solution (Sol-1, Incotec) were added in order to produce pellets of homogeneous size and shape (2.00–2.25 mm slot screen).

Figure 4:
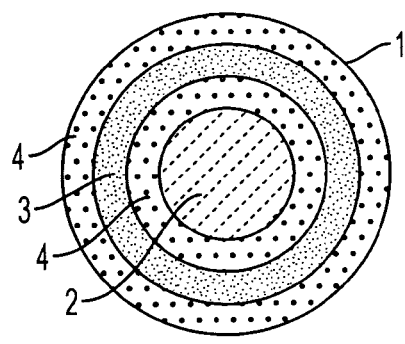

Then, the pellets were dried at a temperature of 60° C. for 45 minutes resulting in pellets as described in FIG. 4.

EXAMPLE 3

Figure 1:
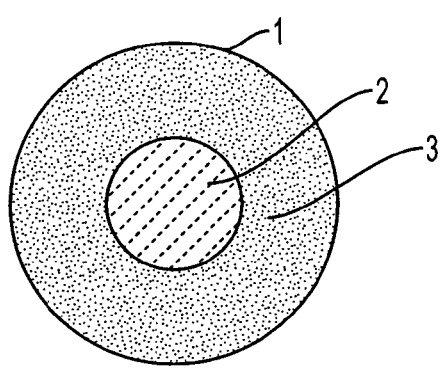

In a fume cupboard at room temperature, 345 g of a commercial coating formulation (Disco L126, Incotec) is mixed with 107 g insecticide formulation Gigant 480FS (DowElanco) and 11.5 g fungicide solution Rovral Aquaflo (Rhone Poulenc). A batch of 1495 gram cauliflower seeds (Brassica oleracea) with a seed-fraction of 1.50–1.75 mmR was killed by means of microwave (300W, 45 min., Samsung M935). The batch was processed according to the standard procedure in a Pancoater (Ramacota-18) with an 18 inch diameter. This procedure entailed that during the entire process the coating formulation was slowly distributed over the seeds by means of an air spray gun while continuously drying (drying temperature=55° C.) resulting in film-coated seeds as described in FIG. 1. The insecticide is comprised in the thin layer of film coating on the outside of the 'dead' seed.

The present invention is not limited to the embodiments mentioned in the above examples. They can be varied in many ways, all deemed within the scope of the appended claims.

What is claimed is:

1. Method for the protection of a germinating seed with a pesticide, characterized in that seed-containing pellets and pesticide-containing pellets are sown as individual pellets at the same time and wherein said pesticide-containing pellet comprises a killed seed as a core wherein said pesticide is located around said core; and wherein said killed seed is killed by gamma waves or microwaves.

2. Method according to claim 1, characterized in that the pesticide-containing pellets have substantially the same shape and size as the seed-containing pellets.

3. Method according to claim 1, characterized in that the pesticide-containing pellets comprise a dose of pesticide that is sufficient for one seed germ.

4. Method according to any of the above claim 1, characterized in that the pesticide-containing pellets contain a filler material.

5. Method according to claim 1, characterized in that the pesticide-containing pellets and the seed-containing pellets have a substantially uniform diameter ranging from 0.5–5 mm.

6. Method for the protection of a germinating seed with a pesticide, characterized in that seed-containing pellets and pesticide-containing pellets are sown as individual pellets at the same time and wherein said pesticide-containing pellet comprises a killed seed as a core wherein said pesticide is located around said core;

wherein said killed seed is killed by gamma waves or microwaves; and wherein said pesticide-containing pellet and seed-containing pellet are sown at a ratio of 1:1.

7. Method according to claim 6, characterized in that the pesticide-containing pellets have substantially the same shape and size as the seed-containing pellets.

8. Method according to any of the above claim 6, characterized in that the pesticide-containing pellets contain a filler material.

9. Method according to claim 6, characterized in that the pesticide-containing pellets and the seed-containing pellets have a substantially uniform diameter ranging from 0.5–5 mm.

* * * * *